US008838205B2

(12) United States Patent
Shoham et al.

(10) Patent No.: US 8,838,205 B2
(45) Date of Patent: Sep. 16, 2014

(54) ROBOTIC METHOD FOR USE WITH ORTHOPEDIC INSERTS

(75) Inventors: Moshe Shoham, Hoshaya (IL); Leo Joskowicz, Jerusalem (IL); Charles Milgrom, Jerusalem (IL); Ziv Yaniv, Jerusalem (IL); Ariel Simkin, Jerusalem (IL)

(73) Assignee: Mazor Robotics Ltd., Caesarea (IL)

( * ) Notice: Subject to any disclaimer, the term of this patent is extended or adjusted under 35 U.S.C. 154(b) by 1975 days.

(21) Appl. No.: 10/517,846

(22) PCT Filed: Jun. 17, 2003

(86) PCT No.: PCT/IL03/00515
  § 371 (c)(1),
  (2), (4) Date: Dec. 29, 2005

(87) PCT Pub. No.: WO03/105659
  PCT Pub. Date: Dec. 24, 2003

(65) Prior Publication Data
  US 2006/0098851 A1  May 11, 2006

Related U.S. Application Data

(60) Provisional application No. 60/389,214, filed on Jun. 17, 2002.

(51) Int. Cl.
  *A61B 5/05* (2006.01)
  (Continued)

(52) U.S. Cl.
  CPC .............. *A61B 17/1703* (2013.01); *A61B 19/50* (2013.01); *G05B 2219/45168* (2013.01); *A61B 17/1725* (2013.01); *A61B 19/22* (2013.01); *A61B 19/2203* (2013.01); *A61B 2019/5238* (2013.01); *A61B 19/201* (2013.01); *A61B 17/1721* (2013.01); *G05B 2219/39011* (2013.01); *A61B 17/1728* (2013.01); *G05B 2219/40267* (2013.01); *A61B 2019/2226* (2013.01); *G05B 19/402* (2013.01); *G05B 2219/49113* (2013.01); *Y10S 128/908* (2013.01); *Y10S 128/922* (2013.01); *Y10S 128/923* (2013.01)
  USPC ........... 600/424; 600/407; 600/437; 600/443; 606/88; 606/130; 128/908; 128/922; 128/923

(58) Field of Classification Search
  CPC ............... A61B 2019/5238; A61B 2019/5466; A61B 6/03; A61B 2019/524
  USPC ......... 600/407, 409, 410, 414, 415, 420, 421, 600/422, 423, 424, 427, 436, 437, 476; 606/88, 130; 128/908, 922, 923
  See application file for complete search history.

(56) References Cited

U.S. PATENT DOCUMENTS 4,465,065 A  8/1984  Gotfried
(Continued)

FOREIGN PATENT DOCUMENTS

| JP | 2001-293004 A | 10/2001 |
|---|---|---|
| WO | 98/04203 A2 | 2/1998 |
| WO | 00-019927 A1 | 4/2000 |

OTHER PUBLICATIONS

Radim Halir et al., Numerically Stable direct least squares fitting of ellipses, Proceedings 6th International Conference Central Europe, Computer Graphics, 1998, pp. 125-132.
(Continued)

*Primary Examiner* — Mark Remaly
(74) *Attorney, Agent, or Firm* — Daniel Feigelson; Fourth Dimension IP

(57) ABSTRACT

A robot-guided system to assist orthopaedic surgeons in performing orthopaedic surgical procedures on pre-positioned inserts, including for the fixation of bone fractures, and especially for use in long bone distal intramedullary locking procedures. The system provides a mechanical guide for drilling the holes for distal screws in intramedullary nailing surgery. The drill guide is automatically positioned by the robot relative to the distal locking nail holes, using data derived from only a small number of X-ray fluoroscopic images. The system allows the performance of the locking procedure without trial and error, thus enabling the procedure to be successfully performed by less experienced surgeons, reduces exposure of patient and operating room personnel to radiation, shortens the intra-operative time, and thus reduces post-operative complications.

18 Claims, 9 Drawing Sheets

(51) Int. Cl.
*A61B 17/17* (2006.01)
*G05B 19/402* (2006.01)
*A61B 19/00* (2006.01)

(56) References Cited

U.S. PATENT DOCUMENTS

| | | | |
|---|---|---|---|
| 4,979,949 A | | 12/1990 | Matsen, III et al. |
| 5,408,409 A | * | 4/1995 | Glassman et al. ............ 600/407 |
| 5,411,503 A | | 5/1995 | Hollstien et al. |
| 5,690,635 A | | 11/1997 | Matsen, III et al. |
| 6,322,567 B1 | * | 11/2001 | Mittelstadt et al. ........... 606/130 |
| 6,423,061 B1 | | 7/2002 | Bryant |
| 6,675,068 B1 | | 1/2004 | Kawasaki |
| 6,690,761 B2 | * | 2/2004 | Lang et al. ....................... 378/56 |
| 6,718,194 B2 | * | 4/2004 | Kienzle, III ................... 600/424 |
| 6,792,335 B2 | | 9/2004 | Ross et al. |
| 6,837,892 B2 | * | 1/2005 | Shoham ........................ 606/130 |
| 2002/0038118 A1 | | 3/2002 | Shoham |
| 2002/0094189 A1 | * | 7/2002 | Navab et al. ....................... 386/4 |
| 2002/0188380 A1 | | 12/2002 | Ross et al. |
| 2004/0133316 A1 | | 7/2004 | Dean |

OTHER PUBLICATIONS

Leo Joskowicz et al., Computers in Imaging and Guided Surgery, Computers in Science and Engineering, 2001, pp. 65-72, vol. 3(5).
Robert J. Brumback, MD., Section III—Regular and Special Features—The Rationales of Interlocking Nailing of the Femur, Tibia, and Humerus, Clinical Orthopaedics and Related Research, Mar. 1996, pp. 292-320, vol. 324, Lippincott-Raven—Publisher.
S. Skjeldal et al., Interlocking Medullary Nails—Radiation Doses in Distal Targeting, Archives of Orthopaedic and Traumatic Surgery, Clinical and Experimental Forum, 1987, pp. 179-181, vol. 106.
Christian Krettek, MD, A Mechanical Distal Aiming Device for Distal Locking in Femoral Nails, Jul. 1999, pp. 267-275, vol. 364.
Leo Joskowicz Ph.D., Fracas: A System for Computer-Aided Image-Guided Long Bone Fracture Surgery, Biomedical Paper, Journal of Computer-Aided Surgery, 1999, pp. 271-288, vol. 3 (6).
Kevin Cleary, Ph.D., et al., State of the Art in Surgical Robotics: Clinical Applications and Technology Challenges, Review Article, Journal of Computer Aided-Surgery, 2001, pp. 312-328, vol. 6 (6).
H. Livyatan et al., Robust Automatic C-Arm Calibration for Fluoroscopy-Based Navigation: A Practical Approach, Proc. of $5^{th}$ Int. Conf. on Meical Image Computing, Oct. 2002, pp. 60-68, Tokyo, Elsevier.
Rafael C. Gonzalez et al., Object Recognition, Chapter 12 of Digital Image Processing, Second Edition, ISBN 0-201-18075-8, 2002, pp. 693-750, Prentice-Hall, Inc, Upper Saddle River, New Jersey, USA.
H. J. Noordmans et al., Detection and Characterization of Isolated and Overlapping Spots, Computer Vision And Image Understanding, Article No. IV970604, Apr. 1998, pp. 23-35, vol. 70, No. 1.
Frederic Devernay et al., A Non-Maxima Suppression Method for Edge Detection with Sub-Pixel Accuracy, Institut National De Recherche En Informatique Et En Automatique (INRIA) Research Report No. 2724, ISSN 0249-6399, Nov. 1995, pp. 1-20, Sophia-Antipolis, France.

* cited by examiner

ROBOTIC METHOD FOR USE WITH ORTHOPEDIC INSERTS

This application is filed per 35 U.S.C. §371 as the national phase of PCT/IL03/00515, filed Jun. 17, 2003, which claims the benefit of provisional application No. 60/389,214, filed Jun. 17, 2002.

FIELD OF THE INVENTION

The present invention relates to the field of the robotic guidance of orthopaedic surgical procedures performed on pre-positioned inserts, and especially for use in the orthopaedic reduction of bone fractures using intramedullary locking procedures.

BACKGROUND OF THE INVENTION

The need for precise, minimally invasive, surgical interventions has resulted in the creation of methods of using computers in conjunction with advanced assistance devices to improve surgical planning and execution. Over the past decade, a variety of such Computer Integrated Surgery (CIS) systems have been developed, with resulting clinical benefits, largely for use in the fields of neurosurgery, laparoscopy, maxillofacial surgery and orthopaedics, as for instance described in the article by L. Joskowicz et al., entitled "Computers in imaging and guided surgery", published in Computers in Science and Engineering, Vol. 3(5), pp 65-72, 2001.

CIS systems can potentially benefit many orthopaedic surgical procedures, including total hip and total knee replacement, pedicle screw insertion, fracture reduction, and ACL (Anterior Cruciate Ligament) ligament reconstruction. These procedures are ubiquitous and are performed in high volume in operating rooms worldwide. They generally involve rigid bone structures that image well, require preoperative planning, and employ instruments and tools, such as implants, screws, drills, and saws that require precise positioning. A number of CIS systems for such procedures are currently in use, such as those described in the book "Computer Assisted Orthopaedic Surgery (CAOS)", edited by L. P. Nolte, and R. Ganz, published by Hogrefe and Huber (1999).

One technique used for fracture reduction is closed intramedullary nailing, and, according to the article by R. J. Brumback, "Regular and Special Features—The Rationales of Interlocking Nailing of the Femur, Tibia, and Humerus", published in Clinical Orthopaedics and Related Research, Vol. 324, pp. 586-651, Lippincott-Raven (1996), it is probably the current routine procedure of choice for reducing fractures of the femur and the tibia. This procedure restores the integrity of the fractured bone by means of a nail inserted in the medullary canal. In most cases, the surgeon inserts lateral proximal and distal interlocking screws, to prevent fragment rotation and bone shortening. Preparation of the bone for distal locking has long been recognized as one of the most challenging steps in the procedure, at least according to prior art methods of performing the procedure. The procedure is performed under X-ray fluoroscopy, which is used to view the position of the bone fragments, the surgical tools and the implants used, in order to determine the position of the holes to be drilled for these screws. Numerous X-ray fluoroscopic images are required for this procedure, since the nail often deforms by several millimeters to conform to the bone canal shape, and the exact position of the distal locking nail holes cannot therefore be determined in advance. According to these prior art methods, the surgeon adjusts the entry point and orientation of the drill, to the best of his judgement and his interpretation of the X-ray images, by repeatedly alternating between anterior-posterior and lateral X-ray fluoroscopic views, such that the drill axis coincides as accurately as possible with the corresponding nail hole axis. Drilling proceeds incrementally, with each advance verified with a new pair of X-ray fluoroscopic images. Once the pilot hole passing through the distal locking nail hole has been drilled in the bone, the locking screws can be inserted and fastened.

Because of the nature of the procedure, depending very largely on the skill of the surgeon, a number of complications can arise, including inadequate fixation, malrotation, bone cracking, cortical wall penetration and bone weakening due to multiple or enlarged pilot holes. Furthermore, it has been reported in the article "Interlocking medullary nails—radiation doses in distal targeting" by S. Skejdal and S. Backe, published in Archives of Orthopaedic Trauma Surgery, Vol. 106, pp 179-181, 1987, that the surgeon's direct exposure to radiation per procedure, using these prior art methods, is 3-30 minutes, depending on the patient anatomy and the surgeon's skill. In general, something between about 30 and 50% of this time is spent on the distal locking process.

Many non-CIS devices have been developed for distal locking, even recently, such as that described by C. Krettek, et al, in the article "A mechanical distal aiming device for distal locking in femoral nails", published in Clinical Orthopaedics, Vol. 384, pp. 267-275, 1999. Examples of such devices and procedures include proximally mounted targeting devices, stereo fluoroscopy, mechanical guides, and optical and electro-magnetic navigation systems that help locate the center of the distal locking nail holes. However, these devices and techniques generally have some disadvantages, for instance that they are only selectively applicable, may be cumbersome and difficult to use, may not be sufficiently accurate, and they thus fail to significantly reduce the likelihood of patient complications.

Fluoroscopy-based CIS navigation systems, such as those described by L. Joskowicz, et al., in the article "FRACAS: A system for computer-aided image-guided long bone fracture surgery", published in "Journal of Computer-Aided Surgery", Vol. 3(6), pp. 271-288, 1999, take the guesswork out of targeting. Such systems enhance, reduce, or altogether eliminate X-ray fluoroscopic images by replacing them with a virtual reality view in which the positions of the bone and the surgeon's instruments are continuously updated and viewed on-screen as they move, using tracking devices and three dimensional registration procedures. They can assist the surgeon in aligning the drill axis with the distal locking nail hole axis to an accuracy of about 1 mm and 1°. However, they do not provide any mechanical guidance for the hand-held drill, which can slip or deviate from its planned trajectory as the drilling proceeds. Thus, even using such prior art CIS navigation systems, the surgical outcome of the procedure is still dependent to an extent on the skill of the surgeon.

Robot-based CIS systems have been developed to assist the surgeon in implementing the preoperative plan by mechanically positioning and sometimes executing the surgical action itself. One such system is described by K. Cleary et al., in the article "State of the art in surgical robotics: clinical applications and technology challenges", published in Journal of Computer-Aided Surgery, Vol. 6(6), pp. 312-328, 2001. The robots are either floor-standing industrial robots, adapted for use in the desired surgical application, or table-mounted custom-designed serial robots. Such robots are generally voluminous and heavy, despite the fact that in such surgical applications, they need to operate with relatively small workloads and work volumes. In such systems, bone immobilization or real-time dynamic tracking are important issues, since the relative configuration of the bone with respect to the robot must be known precisely at all times. This may complicate the registration procedure and may adversely affect the overall system accuracy.

There therefore exists a need in the field of orthopaedic surgery, for a system which overcomes the disadvantages of prior art systems, and enables the automatic alignment of tools required for the procedure, with the bones or inserts involved in the procedure, such that the procedure becomes less dependent on the skill of the surgeon, with a concomitant increase in the success rate of the procedure.

The disclosures of each of the publications mentioned in this section and in other sections of the specification, are hereby incorporated by reference, each in its entirety.

SUMMARY OF THE INVENTION

The present invention seeks to provide a new robotic guidance system, with the robot mounted directly on the bone on which the operation is being performed, or in a configuration which ensures that the robot position has a direct one-to-one relationship with the position of the bone, and which assists the orthopaedic surgeon in performing procedures involving the alignment of surgical tools with features of internally located implants utilized in the performance of the desired orthopaedic procedure. The robot itself is small, and is thus unobtrusive and easily rendered safe for use in the sterile operating room environment. The system significantly reduces the likelihood of complications arising in the procedure, since the surgical tool in use is aligned automatically with its target site, both laterally and angularly. Furthermore, the need for numerous, trial and error, X-ray fluoroscopic images is reduced, thus increasing radiation safety for all involved. The system is particularly suitable for the automatic alignment of a bone drill with predrilled holes present in metallic inserts within or in contact with the patient's bone. One preferred use of such a system is for the robotically-controlled guidance of a target drill to exactly match the position and orientation of the distal locking holes in a pre-inserted intramedullary nail, as used in long bone fracture reduction. The mounting of the robot directly on the bone, and hence also effectively on the nail, which is inserted firmly into the bone, has the advantage that if the nail rotates, the robot moves with it, thus preserving the mutual orientation and position of the guide drill with the distal holes in the nail. If the robot is alternatively mounted directly on the nail, this advantage applies directly.

The system preferably comprises a miniature robot holding a targeting drill guide. The robot, because of its small size and weight, can be mounted directly on the bone on which the desired procedure is being performed. In the case of the long bone intramedullary distal locking procedure, the robot is, according to one preferred embodiment, attached to the proximal nail head. Alternatively and preferably, it is directly mounted laterally on the patient's bone segment distal to the fracture line and proximal to the distal locking nail holes. The targeting drill guide preferably has one or more guide holes for the drill, in accordance with the number of holes to be drilled, and a targeting fiducial marker pattern for use in determining the position and alignment of the targeting drill guide in the X-ray fluoroscopic images taken during the procedure. To obtain accurate registration results using these X-ray fluoroscopic images, camera distortion correction and calibration are performed, preferably using an image calibration ring on the fluoroscopic X-ray C-arm unit.

Using only a small number of lateral X-ray fluoroscopic images, the axis or axes of the targeting drill guide holes are brought into alignment with the axis or axes of the distal locking nail holes, by computing the transformation between them and positioning the robot accordingly. The surgeon can then drill the holes in the bone with confidence that they will be accurately in line with the holes of the insert. Though the term targeting drill is generally used throughout this application, in keeping with the common procedure where a smaller target drill hole is made as a pilot for the correct size drill bore, it is to be understood that the invention is not limited to targeting drilling procedures but is equally applicable to direct drilling of the final hole, where this procedure is followed.

Mounting the robot directly on the nail or on the patient's bone is minimally invasive, eliminates the need for limb immobilization or real-time tracking, and for trial and error positioning, and greatly simplifies registration. The system can potentially reduce intra-operative time, reduce complications associated with malpositioning, and can allow less-experienced surgeons to perform the locking with high success rates.

There is thus provided in accordance with a preferred embodiment of the present invention, a surgical system comprising a robot connected to a bone, with which is associated an orthopaedic insert having at least one predrilled hole for attaching the insert to the bone, a drill guiding plate carried by the robot, the guiding plate having at least one hole for guiding a drill into the bone and through the at least one predrilled hole, an imaging system generating at least one image including the drill guiding plate and the at least one predrilled hole, and a computational system utilizing data from the at least one image to align the robot such that the axis of the at least one hole defined by the drill guiding plate is aligned essentially colinearly with the axis of the at least one predrilled hole defined by the insert.

In the above described system, the axis of the at least one hole defined by the drill guiding plate is preferably aligned essentially colinearly with the axis of the at least one pre-drilled hole both laterally and in angular orientation. The drill guiding plate preferably comprises a plurality of fiducial markers disposed in a predetermined pattern. This plurality of fiducial markers is preferably used to align the drill guiding plate by means of the robot such that it images the drill guiding plate in a fronto-parallel orientation. In any of the above described embodiments of the system, the imaging system is preferably aligned such that it images the at least one predrilled hole in a fronto-parallel orientation. As a result, the computational system may align the robot by utilizing data from only one image of the imaging system.

There is further provided in accordance with yet another preferred embodiment of the present invention, a surgical system as described above, and wherein the robot is directly mounted either on the bone or is attached to an insert associated with the bone. In any of the above described systems, the robot maintains its position relative to the bone such that both tracking of the bone position and immobilization of the bone are obviated.

In accordance with still more preferred embodiments of the present invention, in these surgical systems, the bone may be a long bone, and the orthopaedic insert an intramedullary nail, and the at least one predrilled hole a distal locking hole. In such cases, the robot may be attached to the proximal end of the intramedullary nail.

Alternatively and preferably, the orthopaedic insert may be an externally attached connector plate, and the at least one predrilled hole a connecting hole. In such cases, the bone may preferably be a femur, and the connector plate a percutaneous compression plate, and the connecting hole may then be either such as to accommodate a screw for connecting the plate to the shaft of the femur, or such as to connect a fractured head of the femur to its shaft.

In any of the above embodiments of the surgical system, the imaging system preferably comprises an image intensifier with a calibration ring assembly, adapted to enable at least one of image distortion correction and camera calibration.

There is further provided in accordance with still another preferred embodiment of the present invention, a surgical system as described above, and wherein the robot comprises a miniature parallel robot. Such a robot preferably comprises at least three actuators mounted on a base member, the actuators being configured for at least one of translational and rotational movement.

In accordance with further preferred embodiments of the present invention, there is also provided an imaging system comprising:

a radiation source for illuminating a target to be imaged, the target having at least one predefined hole, a target guide having at least a second predefined hole, whose axis is to be brought into coincidence with the axis of the at least one predefined hole of the target, a robot on which the target guide is mounted, for bringing the axes of the at least one target guide hole and the at least one target hole into coincidence, an image intensifier generating images of the target and the target guide, and a computation system comprising:

a first position localizing module, which computes the position of the at least one target guide hole from an image thereof, a second position localizing module, which computes the position of the at least one target hole from an image thereof, and a registration unit adapted to determine a spatial relationship between the at least one target guide hole and the at least one target hole.

In the above described imaging system, the image intensifier is preferably aligned in a fronto-parallel setup, such that the registration unit determining the spatial relationship between the at least one target guide hole and the at least one target hole, utilizes a two-dimensional image only. In this case, the alignment is adjusted by determining when an image of the at least one target hole has a minimum elliptic shape. The image intensifier preferably incorporates distortion correction and camera calibration functions, or alternatively and preferably, the system also comprises a separate calibration ring assembly for distortion correction and camera calibration.

In the above described embodiments of the imaging system, the target guide preferably comprises a predetermined pattern of fiducial markers, the images of which are utilized by the first position localizing module in the computing the position of the at least one target guide hole.

In the above described imaging system embodiment, the first position localizing module, which computes the position of the at least one target guide hole, preferably comprises (i) a fiducial marker position locator and position template determiner, (ii) an image generator producing a new image of the target guide, comprising the at least one image of the target guide from which the positions of the fiducial markers have been morphologically removed, (iii) a normalized cross correlation calculator for the template at pixel locations with negative values, determining the centers of the fiducial markers, (iv) a fiducial searcher looking in small areas around local maxima found by the normalized cross correlator, and (v) a position locator for the targeting guide localization, from the locations of the fiducials determined in step (iv). The fiducial marker position locator and position template determiner preferably utilizes a Hough transform method, and the position locator preferably utilizes a principal component analysis procedure.

Furthermore, in the above described imaging system embodiments, the second position localizing module, which computes the position of the at least one target hole from an image thereof, preferably comprises (i) a contour locator using an edge detection routine, for determining the longitudinal contours of the target, (ii) a hole searcher, determining the position of holes in an area between the longitudinal contours in an image of the target, using a detector for regions with the maximal number of edge elements in windows of dimensions similar to that of the hole moved over the contour, and (iii) an ellipse fitter for the edge elements in each of the regions detected. The edge detection routine is preferably a Canny edge detector with sub-pixel edge localization.

Additionally, in the above described imaging system embodiments, the registration unit adapted to determine a spatial relationship between the at least one target guide hole and the at least one target hole, preferably comprises an aligner to bring the image intensifier to a fronto-parallel configuration such that the at least one image of the target hole has a minimal elliptic shape, a target guide aligner routine, such that the at least one image of the target guide hole has a minimal elliptic shape, and a target guide lateral translator so that the positions of the axes of the target guide hole and the target hole coincide.

Using the imaging system in the above-described various preferred embodiments, there is further provided a method of bringing the positions of the axes of a hole defined by a target guide and a hole defined by the target into coincidence, comprising the steps of localizing the position of the target guide hole from at least one image thereof, localizing the axis of the target hole from at least one image thereof, and registering the localized target guide hole with the axis of the target hole. An initial step may preferably be performed of image distortion correction and calibration of the imaging system to obtain the images of the target guide hole and the target hole. The individual computing modules of the imaging system embodiments described above operate according to more preferred methods of the present invention, as described in relation to each functional module, and its parts.

BRIEF DESCRIPTION OF THE DRAWINGS

The present invention will be understood and appreciated more fully from the following detailed description, taken in conjunction with the drawings in which.

DETAILED DESCRIPTION OF PREFERRED EMBODIMENTS

Figure 1A:
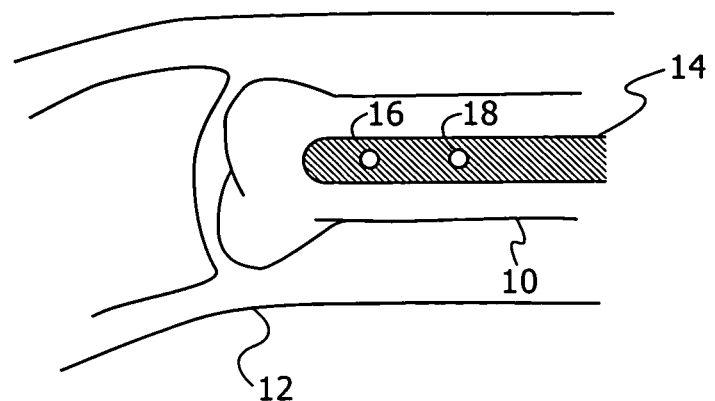
FIGS. 1A and 1B are schematic representations of lateral and frontal views respectively, such as would be obtained by X-ray fluoroscopic imaging illustrating the distal locking stage of the intramedullary nailing procedure.
Figure 1B:
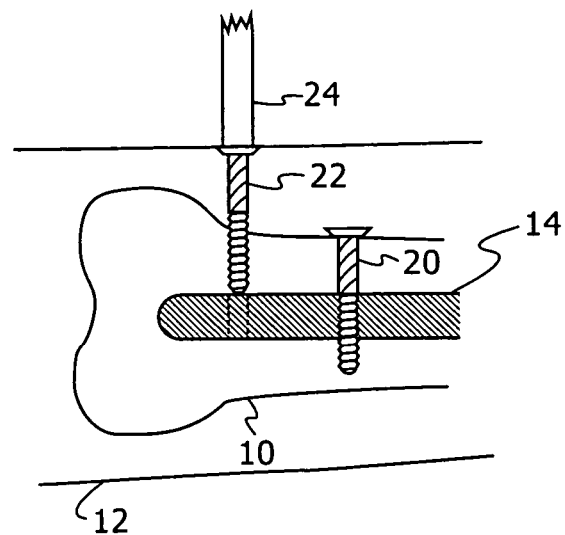

Reference is first made to FIGS. 1A and 1B, which are schematic representations of views that would be obtained by X-ray fluoroscopic imaging, illustrating the distal locking stage of the intramedullary nailing procedure. FIG. 1A is representative of a lateral image and FIG. 1B a frontal image, of the distal part of the femur 10, showing the intramedullary nail 14 with two distal locking nail holes 16, 18. The nail 14 is inserted through a minimal opening, usually in the proximal part of the bone 10, without the need to surgically expose the fracture.

In performing the procedure, the surgeon first reduces the fracture by manipulating the proximal and distal bone fragments through the leg 12 until they are aligned. The surgeon then inserts a guide wire, reams the canal if necessary, and drives in the nail 14. The surgeon then drills the appropriate distal locking nail holes in the bone, opposite the pre-prepared holes 16, 18 in the nail, and inserts lateral proximal and distal interlocking screws 20, 22, to prevent fragment rotation and bone shortening. In FIG. 1B, one locking screw 20 is shown in place, and the second one 22, is shown being fastened by means of a screwdriver 24.

Figure 2:
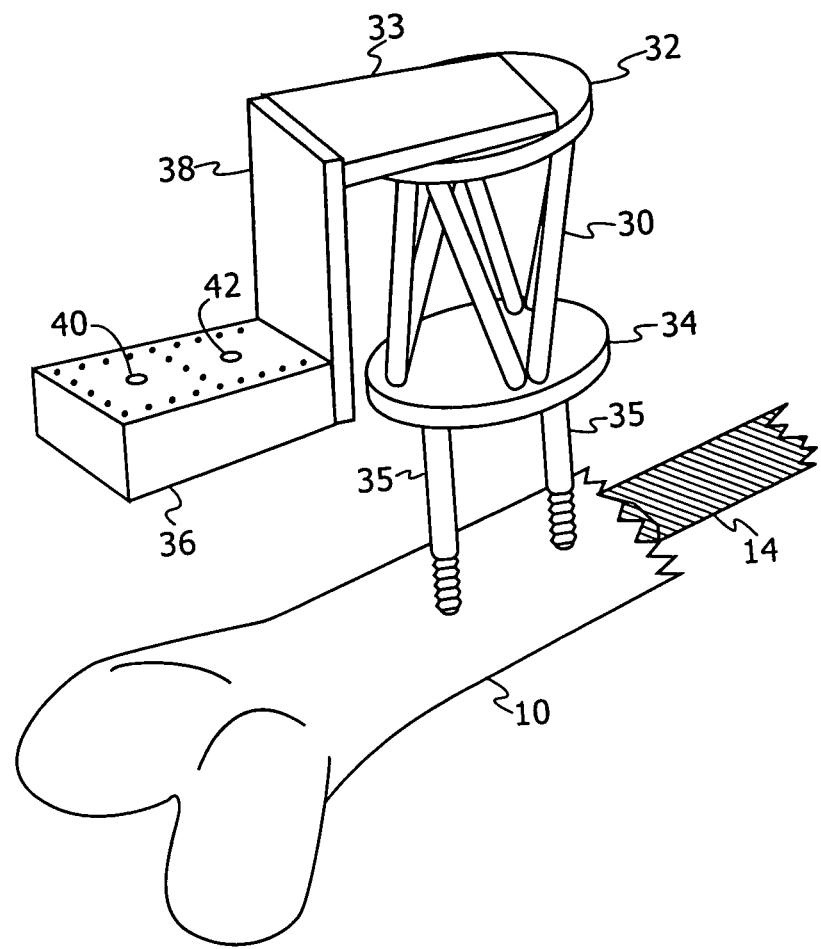
FIG. 2 is a schematic isometric illustration of a robot-based system, constructed and operative according to a preferred embodiment of the present invention, for the precise drilling of the pilot holes for locking screw insertion.

Reference is now made to FIG. 2, which is a schematic isometric illustration of a robot-based system, constructed and operative according to a preferred embodiment of the present invention, for the precise drilling of the pilot holes for locking screw insertion. In the preferred embodiment of FIG. 2, the robot of the system is shown being utilized to position the guide drill axis for drilling through a patient's femur and into the distal locking holes in a pre-inserted intramedullary nail. It is to be understood to those skilled in the art, however, that, with minor modifications, if at all necessary, the system can also preferably be used on any of the other long bones, the tibia, the humerus, the ulna, the radius and the fibula, or for accurately drilling into predisposed orthopaedic inserts other than intramedullary nails, such as connector plates disposed externally to the bone.

In FIG. 2, the patient's femur 10 is shown with the intramedullary nail 14 pre-inserted. The robot 30 is preferably a miniature parallel robot having a base plate 34 for mounting purposes, and a top plate 32 onto which the operating load is attached. The robot shown in the preferred embodiment of FIG. 2 has a height of the order of 70 mm and a weight of about 200 grams. The position and orientation of its top plate 32 can be adjusted and locked by the robot controller to the desired configuration with high accuracy and rigidity. The work volume of the robot is sufficient for the task at hand, which involves motion of a drilling head from a pre-estimated approximate position into the correct position for drilling through the distal locking holes in an intramedullary nail.

The robot carries a guiding assembly, which preferably comprises three components, an adjustable slide head 33, a connecting block 38, and a targeting drill guide 36. The slide head 33 is mounted directly on top of the robot. Its location along the bone long axis can be manually adjusted over a range of typically up to 50 mm., to one of several predetermined positions, as defined by positioning pins and holes in the members of the slide, depending on the application envisaged. The use of predetermined positions is necessary in order to maintain a known predefined registration between the robot frame of reference and the position of the drilling guide hole axes. The pin position selected must be input to the control system so that the actual registration selected is used in the subsequent position calculations. The connecting block 38 and the targeting drill guide 36, are made of radiolucent plastic, since they are visible in the X-ray fluoroscopic images to be taken of the drilling area. The targeting drill guide 38 is preferably in the form of a 40×55×20 mm block, and in the preferred example shown, has two drill guide holes 40, 42, disposed with their axes 30 mm apart, which are predetermined to correspond to the spacing between the centers of the distal locking nail holes. The targeting drill guide 38 is parallel to the robot base 34, and close to the skin of the leg of the patient. The drilling guide has predetermined patterns of fiducial markers that are used for determining its spatial and angular localization in the X-ray fluoroscopic images. In the preferred embodiment shown in FIG. 2, these fiducials are 2 mm. stainless steel spheres arranged in predetermined patterns resembling the letter "A", in its upper and lower surfaces.

There are several methods of mounting the robot on the bone. In the preferred embodiment shown in FIG. 2, the robot base 34 is mounted on two 5 mm diameter by 80 mm length, self-tapping screws, mounted 25 mm apart, which are driven into the distal bone cortex.

Figure 3:
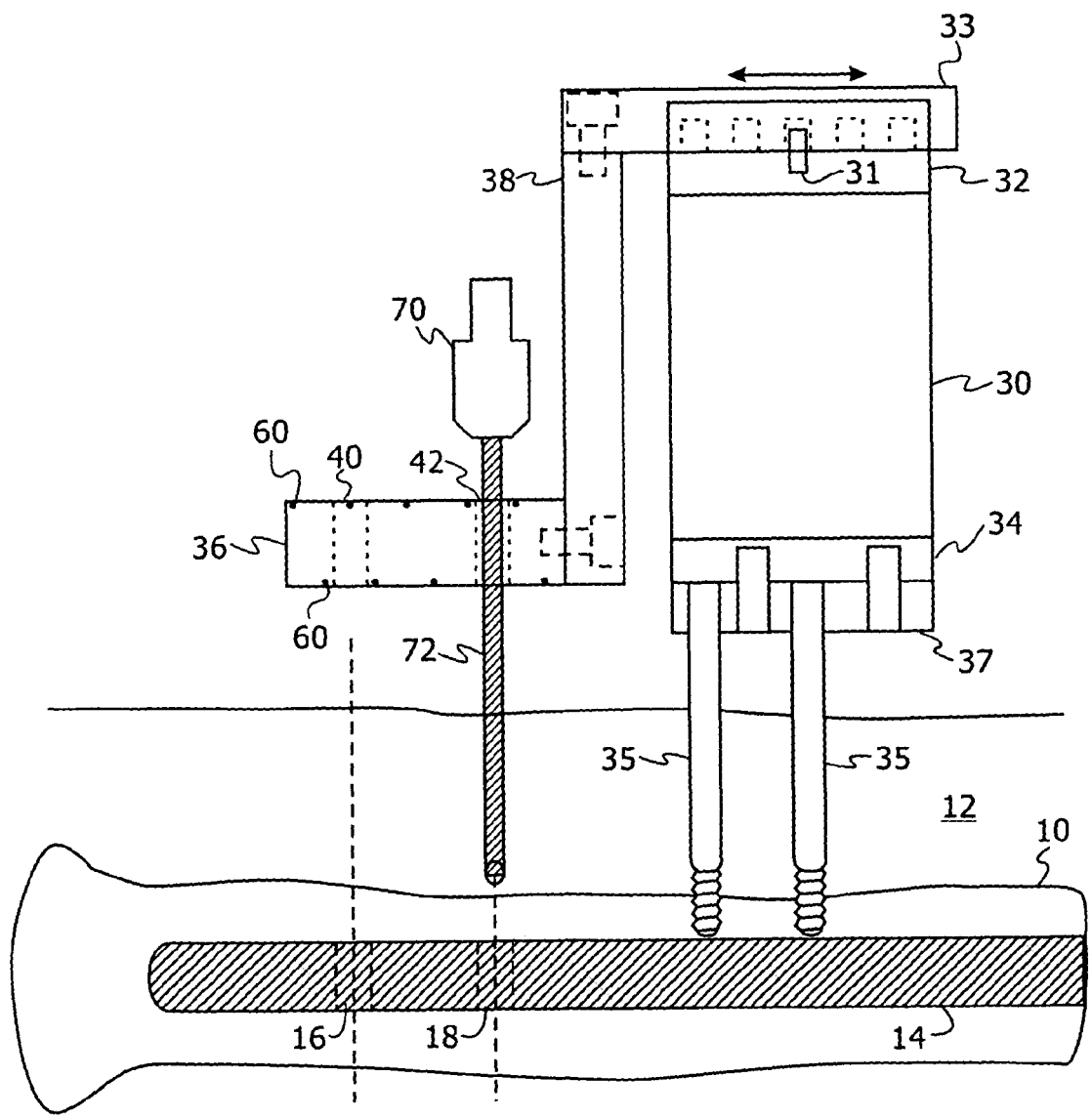
FIG. 3 is a cross-sectional view of the preferred embodiment of FIG. 2, showing some features which are not visible in the isometric view of FIG. 2.

Reference is now made to FIG. 3, which is a cross-sectional view of the preferred embodiment of FIG. 2, showing some features which are not visible in the isometric view of FIG. 2. The set of prepositioning pins and holes 31 between the top plate of the robot 32 and the slide head 33 are shown, though their number and positions in FIG. 3 are meant to be purely illustrative and not limiting. The holes 16, 18, in the intramedullary nail 14 are visible, as are the two layers of fiducial marker spheres 60 in the targeting drill guide plate 36. The drill head 70 is shown with the guide drill bit 72 accurately positioned by the robot over the center of the desired distal locking hole 18 in the nail.

Figure 4:
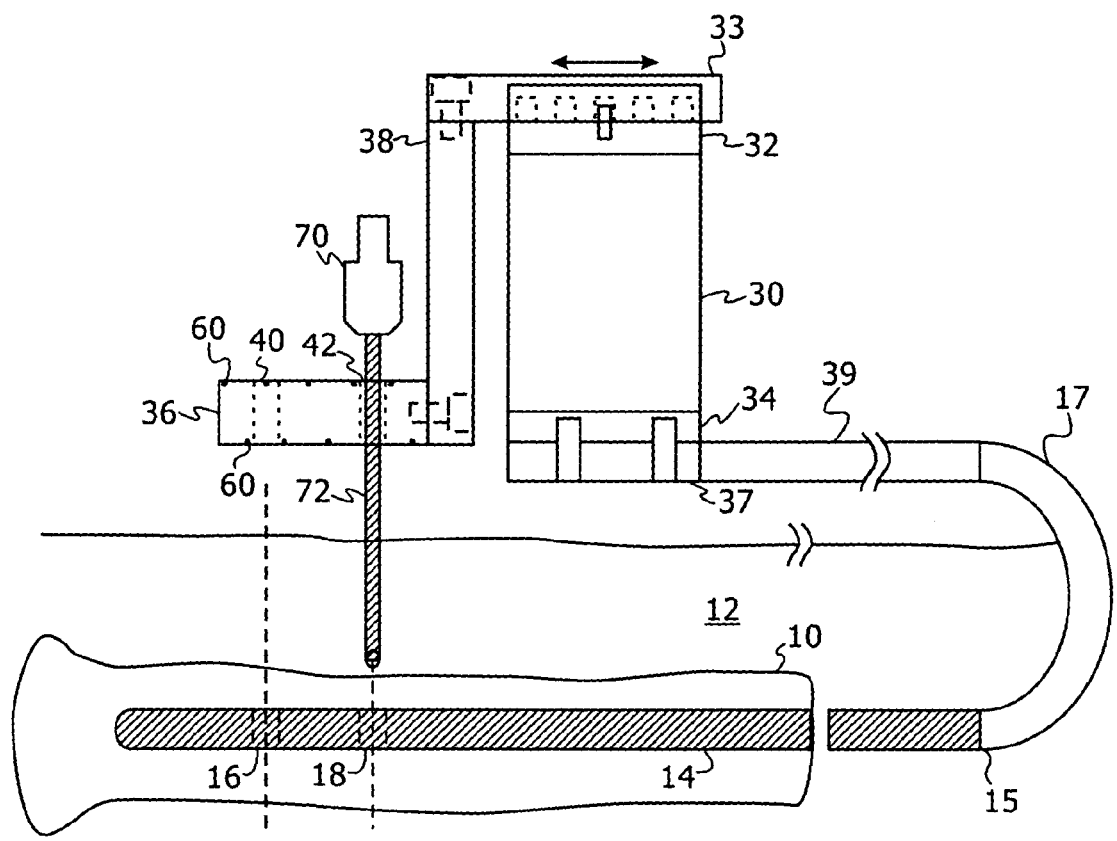
FIG. 4 is a further cross-sectional view of the robot of FIG. 2, showing an alternative and preferred method of mounting the robot to the patient's bone.

Reference is now made to FIG. 4, which is a further cross-sectional view of the robot of the present invention, showing an alternative and preferred method of mounting the robot to the patient's bone. In this embodiment, the robot is fitted with an extended base 39, which is attached by means of a curved support rod 17 to the intramedullary proximal nail head 15. In this embodiment, there is no need for the mounting pins 35 of the embodiment of FIG. 3. All of the other items shown in FIG. 3 are numbered like those shown in the embodiment of FIG. 4. It is to be understood to those skilled in the art that other preferred mounting options besides those shown in FIGS. 3 and 4, are equally applicable for use with the present invention, provided that they provide rigid mounting of the robot relative to the bone being operated on.

Figure 5A:
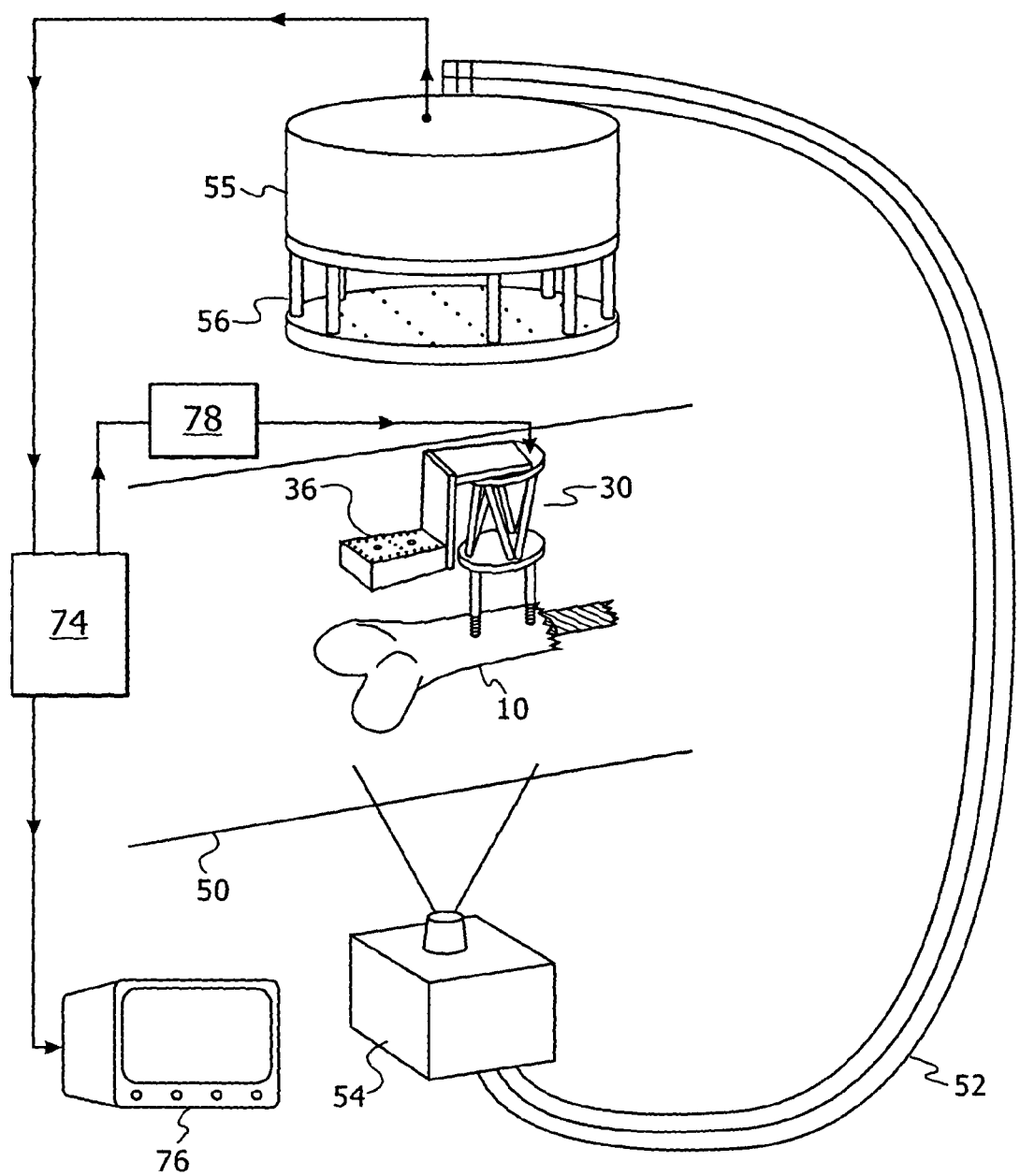
FIG. 5A is a schematic illustration of a complete robot-guided orthopaedic operating system, according to another preferred embodiment of the present invention, incorporating the robot assembly shown in FIG. 2.

Reference is now made to FIG. 5A, which is a schematic illustration of a complete robot-guided orthopaedic operating system, according to another preferred embodiment of the present invention, incorporating the robot assembly shown in FIG. 2. The system preferably includes a stabilized, robotically controlled, targeting drill guide 36, mounted on a miniature robot 30, which is attached to the distal bone fragment 10 of a patient (not shown) lying on a radiolucent operating table 50. The X-ray source 54 is positioned beneath the table, and at the top end of the C-arm 52, the fluoroscopic image intensifier 55 is fitted with an image calibration ring 56, consisting of two parallel plates with embedded fiducials. The images from this image intensifier are directed to a computing system 74 for acquiring fluoroscopic images, either directly in the case of an image intensifier with a digital output port, or through a frame grabber at the input of the computing system in the case of an image intensifier with an analog video output. An image processor analyzes the images obtained, and outputs them for displaying on a monitor 76 to the surgeon. A robot controller card 78 is also incorporated for providing the correct input signals to direct the robot 30, according to command signal outputs generated in the computing system 74.

An image calibration ring 56, such as of the type used in calibration and prior art tracking systems, is preferably attached with clamps to the C-arm image intensifier, and according to a preferred embodiment, has two parallel radiolucent plate targets, spaced 76 mm apart, with 120 embedded fiducial steel balls of 2 mm and 3 mm diameter, arranged in a predetermined asymmetrical pattern. Any suitable pattern which allows for the performance of accurate calibration and registration procedures may preferably be used.

Figure 5B:
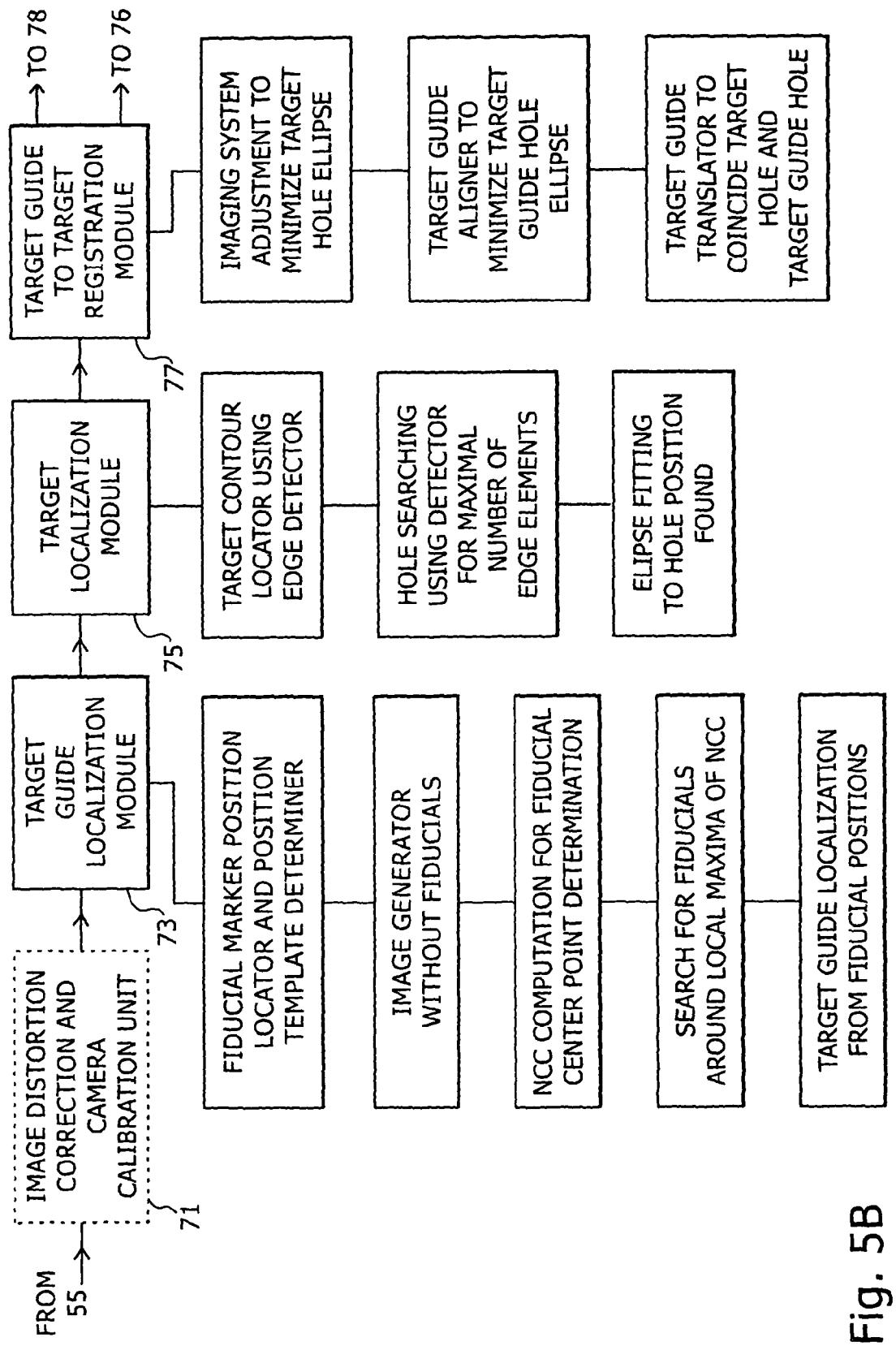
FIG. 5B is a block diagram of the various computing modules which are incorporated, according to a further preferred embodiment of the present invention, into the computing system shown in FIG. 5A.

Reference is now made to FIG. 5B, which is a block diagram of the various computing modules which are incorporated, according to a further preferred embodiment of the present invention, into the computing system 74 shown schematically in FIG. 5A. The output from the fluoroscopic image intensifier 55 is directed into an optional fluoroscopic image distortion correction and calibration unit 71, for use when such a function is not included with the camera system itself. From here, the signal is passed to a target guide localization module 73, which analyzes one or more images containing the target guide, in the case of this preferred embodiment, the drilling guide, such that the target guide localization is known, and to the target localization module 75, which analyzes one or more images containing the target itself, in this embodiment, a distal locking nail hole, to determine the localization of the distal locking nail hole. Though these modules 73, 75, are shown in FIG. 5B operating sequentially, it is to be understood that they can process the signal information simultaneously. Finally, the digital imaging information is passed to a target guide-target registration module 77, which in this preferred embodiment generates a rigid registration between the axes of the targeting drill guide holes and the distal locking nail holes. Beneath each of the three preferred computing modules 73, 75 and 77 of the computing system 74, there are shown implementation steps or units, according to one preferred embodiment of the present invention, though it is to be understood that alternative individual steps which provide the same end registration result could be substituted for any of the propose functional units shown. A full description of the functional performance of each of these units is given hereinbelow. The computing system 74 and its separate modules is designed to be robust, accurate, and to function correctly even with fiducial occlusions in the images, as described more fully hereinbelow.

An outline of a preferred surgical protocol, and system operational procedure to perform it, is as follows. Once the fracture has been reduced and the nail 14 has been inserted to its desired position, the image calibration ring 56 is mounted on the fluoroscopic C-arm image intensifier 55, as shown in FIG. 5A. Using a distal, lateral fluoroscopic image showing the distal locking nail holes, the surgeon determines the location of the self-tapping screws 35 on which the robot is to be mounted. Their axes should be roughly parallel to the distal nail hole axes, and preferably 40 to 80 mm proximal to them. Two parallel pilot holes, preferably approximately 30 mm apart and along the axis of the nail, are then drilled by the surgeon, preferably with the help of a hand-held jig. The self-tapping screws are then fastened, and the robot base mounted on them. The position of the targeting drill guide mounted on the robot top, relative to the distal locking nail holes, is roughly adjusted between its predefined pin positions so that the drill guide holes are approximately above the distal locking nail holes. The orientation of the C-arm is then preferably adjusted by the X-ray technician, until it is determined that the distal locking nail holes are imaged as optimally as possible as circles, rather than ellipses. This indicates that the C-arm imaging axis is parallel with the distal locking hole axes, in what is known as the fronto-parallel set up. In order to increase the precision of the procedure, the determination of the closeness of the nail hole images to a circular shape is preferably performed by the system image processing software, rather than by means of a visual estimation by the X-ray technician. The computing system then determines the relative position of the targeting drill guide with respect to the distal locking nail hole axes, and computes the transformation required so that the targeting drill guide hole axes and the distal locking nail hole axes coincide.

The controller moves the robot according to this computed transformation, and locks the robot with the targeting drill guide holes co-linear with the nail holes. The surgeon then preferably inserts a K-wire in each drill guide hole, and verifies with a new pair of X-ray fluoroscopic images their correct alignment with respect to the distal locking nail hole centers. The surgeon proceeds to drill the screw holes, removes the robot base from its mounting screws, fastens the lateral locking screws into the newly drilled holes, such that they pass exactly through the distal locking nail holes and firmly lock the intramedullary nail to the bone, and then completes the surgery according to the standard protocol.

The preferred procedure described above requires the accurate registration of the targeting drill guide axes with the distal locking nail hole axes, by means of image processing of the X-ray fluoroscopic images obtained, and the use of registration algorithms to define the mutual spatial relation between the targeting drill guide and the locking nail holes. The registration procedure preferably uses spherical fiducial markers, as their centers can readily be located accurately by well-known image processing techniques. The algorithm preferably provides a registration error estimate and notifies the surgeon when the registration cannot be performed because of poor image quality or because of an excessive number of fiducial occlusions.

Figure 6:
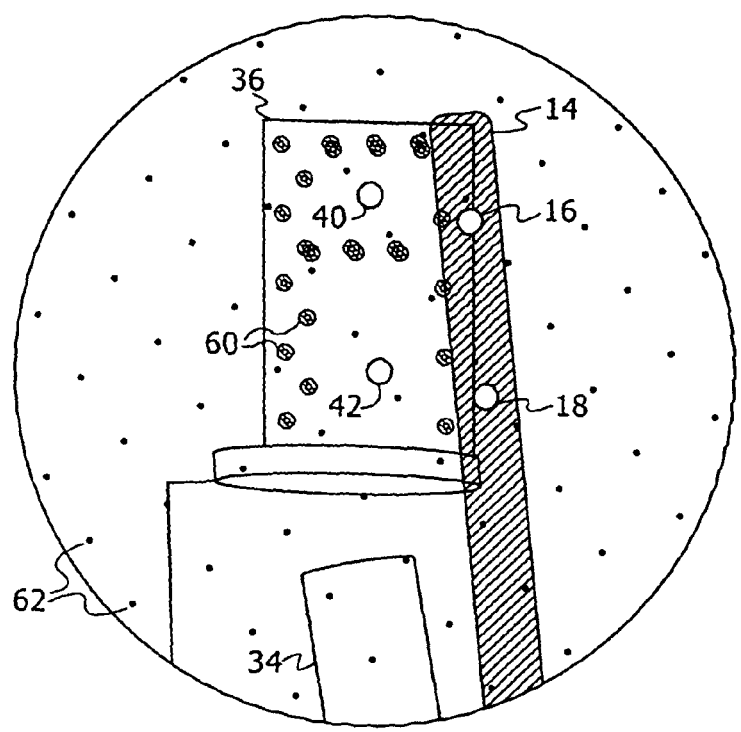
FIG. 6 is a schematic representation of an X-ray fluoroscopic image, showing the targeting drill guide and the distal end of the intramedullary nail with the two distal locking holes.

Reference is now made to FIG. 6, which is a schematic representation of a typical X-ray fluoroscopic image, taken at the initial approximate estimated location of the targeting drill guide, showing the nail 14, the robot base 34, and the targeting drill guide 36. Two sets of fiducials are visible, the set 60 within the targeting drill guide, and the set 62 within the image calibration ring. A few fiducial occlusions, which are due to overlap with other fiducials or other objects, generally always occur. The desired accuracy of the lateral alignment of the drilling guide hole axes 40, 42, is that they should be within ±1 mm of the corresponding nail hole centers 16, 18 in the plane perpendicular to the guide hole axes, and the drilling axis angular deviation should preferably be within ±0.5° of the nail hole axes. These tolerances are required to ensure that the locking screws can be readily inserted without interference into the distal locking nail holes.

In order to achieve this accuracy, according to a further preferred embodiment of the present invention, a model-based method generally consisting of four main steps is used:

(a) X-ray fluoroscopic image distortion correction and camera calibration;
(b) targeting drill guide localization;
(c) distal locking nail hole axes localization; and
(d) registration.

It is to be understood that even though the model-based method is described below as applied to the orthopaedic system described in the preferred embodiments of the present invention, the method is generally applicable to any imaging system application, whether medical, industrial or scientific, where a predefined feature of an image of a target must be made to coincide with a similar predefined feature in an image of a target guide. One common application of such a system is when the predefined features are holes, and the system is utilized for the lining up of a target guide hole in an image, with a hole in an image of the intended target itself. A computing system for performing such a lining-up procedure is described in FIG. 5B hereinabove.

Modern C-arm X-ray fluoroscopic imaging systems are often provided with a built-in distortion correction and calibration capability, such that step (a) of this preferred method may be optionally pre-supplied by such a system.

A brief description of each step follows.
(a) Distortion Correction and Camera Calibration.

A robust automatic C-arm calibration algorithm is provided that includes fiducial localization, distortion correction and camera calibration. The algorithm has been described in the article by H. Livyatan, et al., entitled "Robust automatic C-arm calibration for fluoroscopy-based navigation: a practical approach", in the Proceedings of the 5th International Conference on Medical Image Computing and Computer-Aided Intervention, MICCAI 2002, October 2002, Tokyo, Japan, Elsevier Science Publishers, Amsterdam. This novel algorithm computes the distortion correction and camera calibration parameters from an X-ray fluoroscopic image in three steps:

(i) The algorithm first locates the projections of the image calibration ring fiducials and pairs them with their known spatial location in the pattern;
(ii) the distortion correction parameters are next computed; and
(iii) finally the calibration parameters themselves are computed.

Accurate and robust localization of the fiducials and their pattern is an important step, since all other parameters depend on it to provide accuracy. Use of this algorithm allows the attainment of submillimetric accuracy for the combined dewarping and camera calibration, even when only some of the fiducials are detected.

(b) Targeting Drill Guide Localization.

Figure 7:
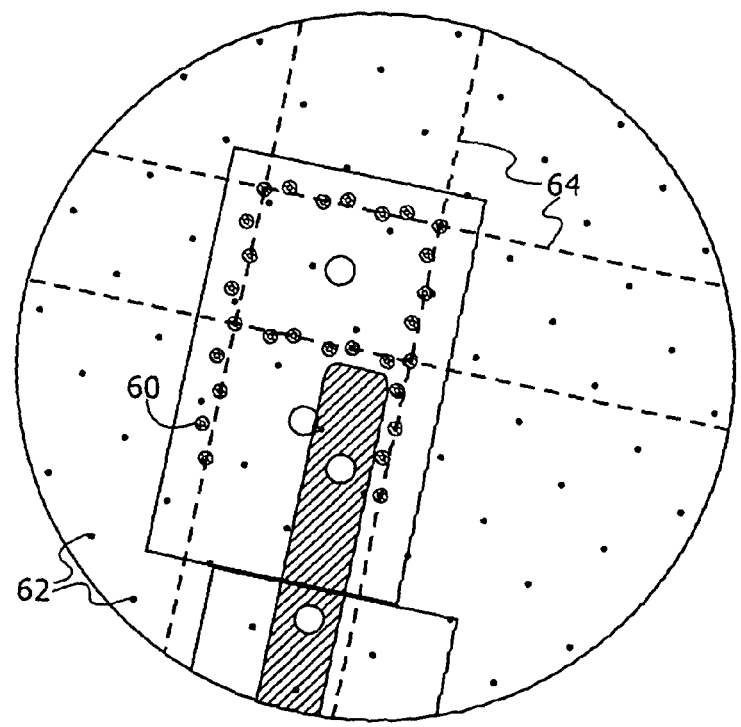
FIG. 7 is a schematic representation of another X-ray fluoroscopic image similar to that of FIG. 6, but showing superimposed fiducial pattern calculation lines to illustrate the method by which the localization of the targeting drill guide is determined.

Reference is now made to FIG. 7, which is a schematic representation of another X-ray fluoroscopic image showing the targeting drill guide, with superimposed fiducial pattern calculation lines 64, to illustrate the method by which the localization of the targeting drill guide is determined.

Targeting drill guide localization is performed by identifying the fiducials 60 and the pattern 64 which they form. In this preferred embodiment of the present invention, the targeting drill guide contains 28 spherical metal balls of 2 mm diameter, asymmetrically distributed in the form of an "A", disposed on two parallel planes 20 mm apart, one in the top surface of the targeting drill guide and the other in the bottom surface. The targeting drill guide pattern preferably used for the registration procedure consists of two orthogonal pairs of parallel lines 64. Since the fiducials are spheres, they appear as circles in the fluoroscopic image. The white dots inside the spheres show the localization of their centers. However, some of the spheres might be occluded, since the dewarping and calibration fiducials 62 and the nail 14 are also present in the image. Using the localization algorithm of the present invention, three fiducials per line are sufficient to determine the location of the line with an accuracy sufficient to meet the above-mentioned requirements for the determination of the position of the drill guide holes.

The localization algorithm, according to this preferred embodiment of the present invention uses the following four steps:

(i) Salient circles are detected using the Hough transform, and a circle template is inferred from them.
(ii) A new image is generated, comprising the original image from which the fiducials have been morphologically removed.
(iii) The Normalized Cross Correlation (NCC) value, also known as the Pearson correlation coefficient, of the circle templates at pixel locations with negative values, is computed, to determine the centers of the fiducial spheres. This procedure is well known, such as is described in Chapter 12 of the book "Digital Image Processing", by R. C. Gonzalez and R. E. Woods, Prentice Hall, 2002. Since the fiducials appear darker than the background, these locations constitute possible locations for the fiducials.
(iv) A search for fiducials is conducted in a small area around the local maxima of the NCC, using one of the methods known in the art, such as, for example, the detection and characterization technique described by H. J. Noordmans H. J. et al., in the article "Detection and characterization of isolated and over-lapping spots", published in Computer Vision and Image Understanding, Vol. 70(1), 1998. This procedure enables detection of most of the fiducials, including those with partial occlusions, but not those totally occluded. The major and minor axes of the targeting drill guide pattern are then determined from the fiducial locations, preferably using Principal Component Analysis (PCA), or any other suitable calculation routine.

(c) Distal Locking Nail Holes' Axes Localization

Figure 8:
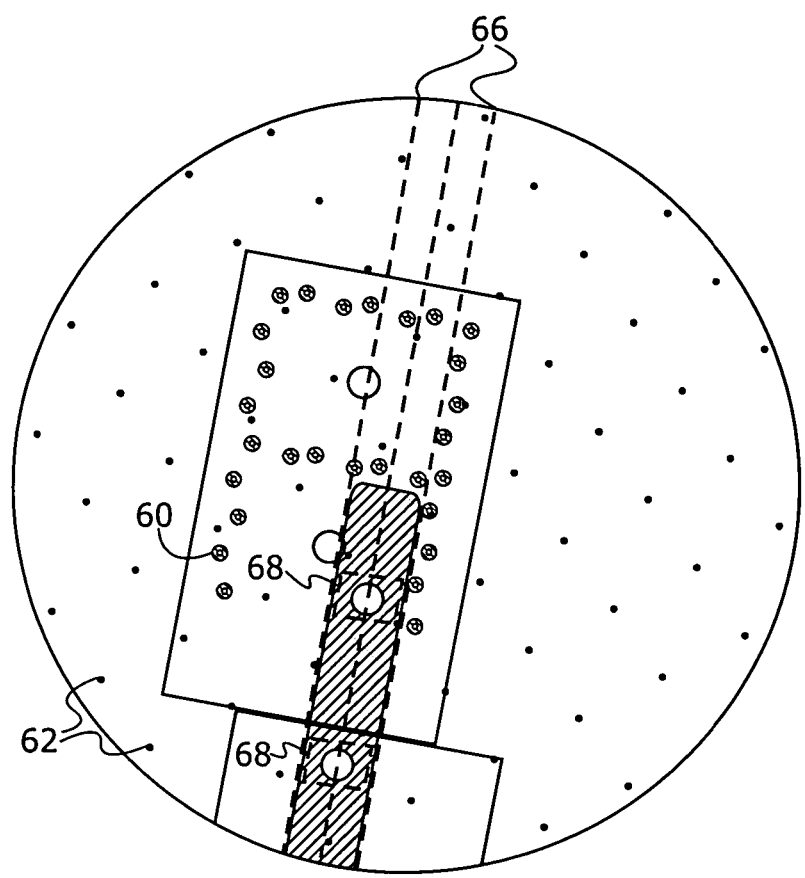
FIG. 8 is a schematic representation of another X-ray fluoroscopic image, similar to that of FIG. 6, but showing superimposed nail longitudinal contour lines to illustrate the method by which the localization of the distal locking holes is determined.

Reference is now made to FIG. 8, which is a schematic representation of another X-ray fluoroscopic image, showing the nail with its distal locking holes and with superimposed nail longitudinal contour lines 66, to illustrate a preferred method by which the localization of the distal locking holes is determined.

The location of the distal locking nail holes in the X-ray fluoroscopic image is preferably determined by first locating the longitudinal contours 66 of the nail, and then locating the holes from their expected position with respect to the contour. To locate the nail longitudinal contours 66, according to a preferred embodiment of the present invention, the Canny edge detector with sub-pixel edge localization, such as that described by F. Devernay, in "A Non-maxima suppression method for edge detection with sub-pixel accuracy", INRIA Research Report No. 2724, Sophia-Antipolis, France, November 1995, is applied to the image. A 3-D Hough transform is then preferably applied to the image data, whereby the nail is modeled as a band consisting of two parallel lines 66 with a known distance between them. The Hough transform voting scheme is constrained so that pixels which are on parallel lines only cast their vote if the gray level values between them are lower than the gray level values outside the band. It is to be understood that this scheme is only one possible method for defining the nail contours, and that other edge detection algorithms, as known in the art, may equally be employed for identifying the nail contours.

Having found the nail's longitudinal contours 66, the algorithm now searches for holes in the area of the image contained between the two lines representing the contour in a 2-D view. The search is performed by moving a virtual parallelepiped window, whose lateral dimensions are equal to the nail width, along the nail's medial axis. The algorithm determines the two locations 68 containing the maximal number of edge elements, which thus correspond to the locations of the distal locking nail holes. An ellipse is then fitted to the edge elements at these locations, such as by means of the algorithm described in the article by R. Halir and J. Flusser, entitled "Numerically stable direct least squares fitting of ellipses", published in Proceedings of the 6th International Conference in Central Europe on Computer Graphics and Visualization (WSCG), pp. 125-132, 1998.

(d) Registration

The distal locking nail holes are modeled as circles, and the X-ray fluoroscopic camera as a pinhole camera. According to this model, the circles in space are mapped to circles in the image when the camera viewing direction is perpendicular to the plane of the circle. This requires a fronto-parallel imaging setup. The use of the fronto-parallel setup, enables the registration procedure of this preferred method of the present invention, to be performed from single 2-dimensional images. To achieve this setup, the X-ray technician images the nail in several orientations until the distal locking nail holes appear as close as possible to circles. The measure of hole circularity is the aspect ratio of the ellipse which is fit to the data points of the edge elements of the holes, as determined in step (c) above. Once a ratio close to unity is achieved, the closeness to unity being decided by a predetermined condition dependent on the accuracy practically required, the targeting drill guide is introduced into the imaging field of view, and an additional image is acquired. The rigid transformation between the drill guide hole axes and the distal locking nail hole axes is computed by the following method. Since the targeting drill guide is pre-calibrated, in that the drill guide dimensions are known, and the mounting position of the slide head of the drill guide relative to the robot top is known, the transformation from the robot coordinate system to the targeting drill guide is also known. The transformation between the targeting drill guide and the fluoroscopic C-arm camera is determined from the extrinsic camera parameters and the known geometry of the targeting drill guide. In order to bring the drill guide hole axes and the distal locking nail hole axes into coincidence, the robot is first orientated so that the drill guide hole axes are aligned with the camera axis, as described above, and is then translated laterally according to the above-described computation, until the centers of the targeting drill guide hole axes and the distal locking nail hole axes coincide. The robot is such as to provide sufficient degrees of freedom of movement to allow alignment both in the lateral plane, as well as the required angular alignment.

Though the system of the present invention, and the use thereof has been described hereinabove by means of its preferred application to the drilling of pilot holes for distal locking screws in long bone intramedullary nailing surgery, it is to be understood that this is only one example of the uses of the system of the present invention. The robot-guided system can be used to assist orthopaedic surgeons in performing other orthopaedic surgical procedures involving pre-positioned bone inserts which have pre-drilled holes for attachment to the bone undergoing the procedure, and the holes are invisible to the surgeon's eye.

Figure 9:
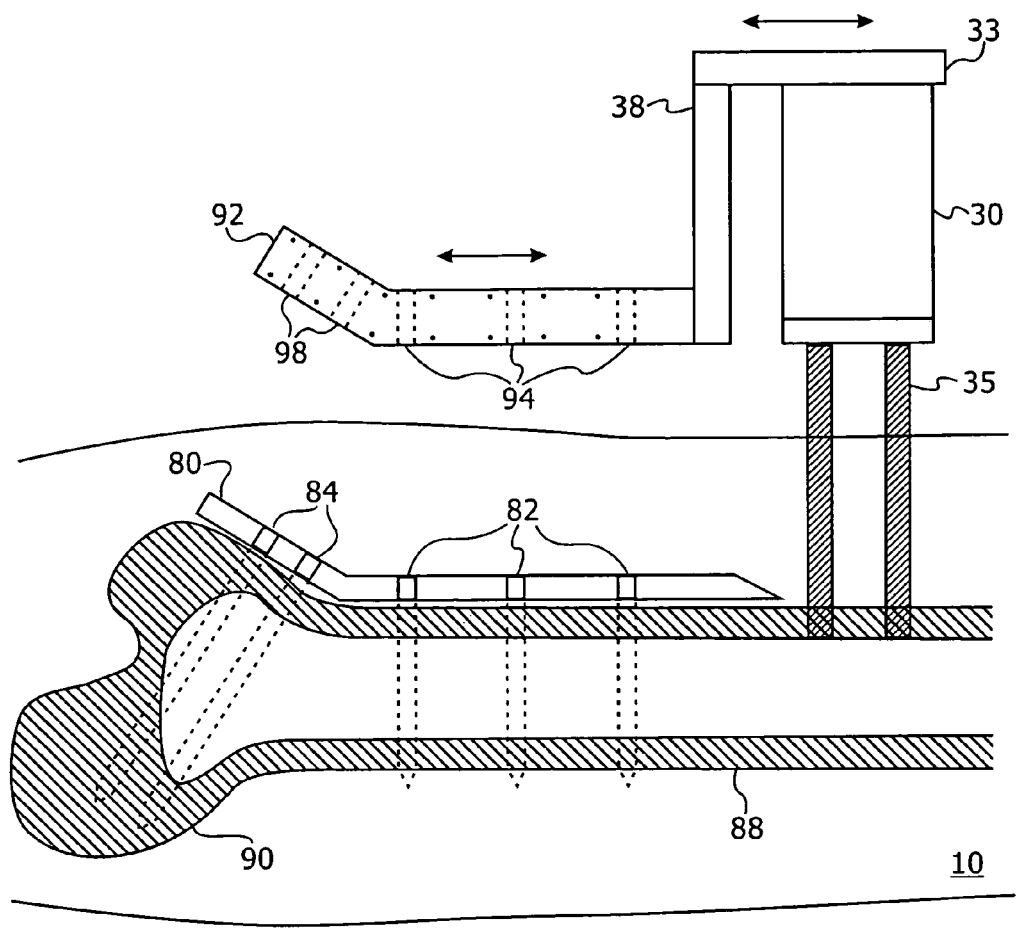
FIG. 9 is a schematic cross sectional view of a robot-based system, similar to that shown in FIG. 2, but being used for the connection of a fractured neck of the femur to the shaft by means of robotic-positioned drilling through a connector plate.

As an example of another preferred application of the system of the present invention, reference is now made to FIG. 9, which is a schematic cross sectional view of a connector plate 80 as used in the connection of a fractured neck of the femur to the bone shaft 88. The connector plate 80 generally has three predrilled holes 82 perpendicular to the shaft, for connection of the plate to the bone shaft 88, and two predrilled holes 84, at an oblique angle, generally of 140° to the plate, for connection of the fractured spherical head of the femur 90. In the prior art, such as is described in U.S. Pat. No. 4,465,065 to Y. Gotfried for "Surgical Device for Connection of Fractured Bones", such a connector plate 80 is inserted percutaneously, through a minimal incision, and is slid into place along the shaft by means of a two armed handle device attached to the rear end of the connector plate. The front end of the connector plate has a chiseled cutting edge to enable easy insertion. Guide tubes are attached to holes in one arm of the device and extending to the predrilled fixing holes in the connector plate. Drilling into the bone parts is performed using these tubes as guides. However, this procedure involves numerous X-ray fluoroscopic images, and insertion of the connector plate using the handle device is not always simple to perform.

Using the robot guided system of the present invention, with the robot 30 mounted on the femur by means of its mounting screws 35, it becomes feasible to perform the insertion of the connector plate, and to accurately drill the connecting screw holes without the use of the prior art handle arm arrangement. A minimal number of X-ray fluoroscopic images are required, first of all to ensure that the plate is inserted with its obliquely aligned holes 84 correctly positioned opposite the femur head. The drilling guide 92 is then aligned with its perpendicular drill guide holes 94 opposite the corresponding holes 82 in the connector plate 80, to the required accuracy, by means of the preferred methods and registration procedures of the present invention, as described hereinabove. The drilling guide plate 92 is, however, different from that used in the intramedullary locking procedure, in that it preferably has a second angled part connected at an angle of 140° to the part parallel to the femur shaft, such that each part is parallel to the corresponding part of the connecting plate. The adjustable slide head 33 is moved such that the angled part of the drilling guide is aligned with its drilling holes 96 approximately opposite the angled holes 84, and the robotic alignment procedure is repeated with the C-arm suitably aligned so as to generate the appropriate fluoroscopic images down the obliquely angled holes, such that they too can be accurately drilled. Alternatively and preferably, the previously used straight drilling guide plate can be used, and the robot tilted at the predetermined angle such that the drilling plate is approximately parallel to the angled part of the connector plate.

It is to be understood by one of skill in the art that the robotic system of the present invention, and the associated methods of use thereof, are not limited to the two preferred applications described hereinabove, but can be used for similar procedures, where the drilling of holes is required into existing pre-drilled holes in orthopaedic inserts inaccessible to the surgeon's eye. Furthermore, the computing system and associated algorithms described hereinabove are understood to be generally applicable to any imaging system application, where a predefined feature of an image of a targeting guide must be brought to coincide with a similar predefined feature in an image of the intended target itself.

It is appreciated by persons skilled in the art that the present invention is not limited by what has been particularly shown and described hereinabove. Rather the scope of the present invention includes both combinations and subcombinations of various features described hereinabove as well as variations and modifications thereto which would occur to a person of skill in the art upon reading the above description and which are not in the prior art.

We claim:

1. A method comprising:
   providing a target orthopedic insert having at least one target hole for attaching said insert to a bone;
   attaching a robot to said bone;
   providing a target guide comprising a predetermined pattern of fiducial markers, and having at least one target guide hole;
   mounting said target guide on said robot;
   obtaining at least one image of at least part of said predetermined pattern of fiducial markers, such that the position of said target guide hole is localized from said at least one image;
   obtaining at least one image of said at least one target hole, such that the axis of said at least one target hole can be localized from said at least one image thereof; and
   registering said at least one image of said at least one localized target guide hole with said at least one image of said localized target hole such that the spatial relationship between said at least one target hole and said at least one target guide hole is determined; and
   utilizing said robot to align the axes of said at least one target guide hole with said at least one target hole.

2. The method of claim 1, and also comprising the initial step of image distortion correction and calibration of the imaging system utilized to obtain said images of said target guide hole and said target hole.

3. The method of claim 1, wherein said localizing the position of said target guide hole from said at least one image of at least part of said predetermined pattern of fiducial markers comprises the steps of:
   (i) detecting the positions of said fiducial markers and inferring a template from their positions;
   (ii) generating a new image of said target guide, comprising said at least one image of said target guide from which said positions of said fiducial markers have been morphologically removed;
   (iii) computing a normalized cross correlation value of said template at pixel locations with negative values to determine the centers of said fiducial markers;
   (iv) searching for fiducials in a small area around local maxima of said normalized cross correlation; and
   (v) determining the position of said targeting guide from the locations of said fiducials determined in step (iv).

4. The method of claim 3, wherein said step of detecting the positions of said fiducial markers is performed using a Hough transform.

5. The method of claim 3, wherein said step of determining the position of said targeting guide from the locations of said fiducials is performed using a principal component analysis procedure.

6. The method of claim 1, wherein said localizing the axis of said target hole from at least one image thereof is performed by the steps of:
   (i) locating the longitudinal contours of said target using an edge detection routine;
   (ii) searching for a hole in an area between said longitudinal contours in an image of said target by detecting regions with the maximal number of edge elements in windows of dimensions similar to that of said hole moved over said contour; and
   (iii) fitting an ellipse to said edge elements in each of said regions detected.

7. The method of claim 6 wherein said edge detection routine is a Canny edge detector with sub-pixel edge localization.

8. The method of claim 1, wherein said registering said at least one image of said at least one target guide hole with said at least one image of said target hole is performed by the steps of:
   adjusting the imaging system used to obtain said images to a fronto-parallel configuration such that said at least one image of said target hole has a minimal elliptic shape;
   aligning said target guide such that said at least one image of said target guide hole has a minimal elliptic shape; and
   translating said target guide laterally so that the positions of the axes of said target guide hole and said target hole coincide.

9. A method comprising:
   providing a target orthopedic insert having at least one predrilled hole for attaching said insert to a bone;
   attaching a robot to said bone;
   providing a drill guiding jig having an array of fiducial markers arranged in a predetermined pattern, and at least one guide hole for guiding a drill into said bone and through said at least one predrilled hole;
   mounting said drill guiding jig on said robot;
   obtaining at least one image of said drill guiding jig and said insert, said at least one image including at least part of said array of fiducial markers on said drill guiding jig, and said at least one predrilled hole in said insert;
   determining the pose of said robot from information regarding said array of fiducial markers in said at least one image;
   determining the position of said at least one predrilled hole from said at least one image; and
   directing said robot such that the axis of said at least one guide hole is aligned essentially collinearly with the axis of said at least one predrilled hole in said insert.

10. The method of claim 9, wherein said robot aligns said axis of said at least one guide hole with the axis of said at least one predrilled hole in said insert both laterally and in angular orientation.

11. The method of claim 9, wherein said robot system aligns said drill guiding jig such that it images said drill guiding jig in a fronto-parallel orientation.

12. The method of claim 9, wherein said at least one image is aligned such that said at least one predrilled hole is in a fronto-parallel orientation.

13. The method of claim 9, wherein said robot is attached to said bone by means of said insert.

14. The method of claim 9, wherein said attachment of said robot to said bone ensures that said robot maintains its position relative to said bone such that neither tracking of said bone position nor immobilization of said bone is required.

15. The method of claim 9, wherein said bone is a long bone, said orthopedic insert is an intramedullary nail, and said at least one predrilled hole is a distal locking hole.

16. The method of claim 9, wherein said orthopedic insert is an externally attached connector plate, and said at least one predrilled hole is a connecting hole.

17. The method of claim 16, wherein said bone is a femur, said connector plate is a percutaneous compression plate, and said connecting hole accommodates a screw for connecting said plate to the shaft of said femur.

18. The method of claim 16, wherein said bone is a femur, said connector plate is a percutaneous compression plate, and said connecting hole accommodates a screw for connecting a fractured head of said femur to its shaft.

\* \* \* \* \*